(12) United States Patent
Kim et al.

(10) Patent No.: US 8,609,861 B1
(45) Date of Patent: Dec. 17, 2013

(54) HEXAAZA [3.3.3] PROPELLANE COMPOUNDS AS KEY INTERMEDIATES FOR NEW MOLECULAR EXPLOSIVES AND A METHOD FOR PREPARING THE SAME

(71) Applicant: Agency for Defense Development, Daejeon (KR)

(72) Inventors: Young Gyu Kim, Seoul (KR); Jin Seuk Kim, Daejeon (KR); Kyoo Hyun Chung, Incheon (KR); Moon Yong Shin, Seoul (KR); Seung Hee Kim, Daejeon (KR); Tae Hwan Ha, Seoul (KR); Hye Ryoung Lee, Seoul (KR); Myeong Hak Kim, Seoul (KR)

(73) Assignee: Agency for Defense Development, Daejeon (KR)

( * ) Notice: Subject to any disclaimer, the term of this patent is extended or adjusted under 35 U.S.C. 154(b) by 0 days.

(21) Appl. No.: 13/652,281

(22) Filed: Oct. 15, 2012

(30) Foreign Application Priority Data

Aug. 3, 2012 (KR) ........................ 10-2012-0085155

(51) Int. Cl.
*C07D 487/18* (2006.01)
*C07D 487/04* (2006.01)

(52) U.S. Cl.
USPC .................................... 548/302.1; 548/303.4

(58) Field of Classification Search
USPC ............................................ 548/302.1, 303.4
See application file for complete search history.

(56) References Cited

U.S. PATENT DOCUMENTS 5,061,330 A 10/1991 Reed, Jr. et al.
6,736,913 B1 5/2004 Hatch

*Primary Examiner* — Laura L. Stockton
(74) *Attorney, Agent, or Firm* — Harness, Dickey & Pierce, P.L.C.

(57) ABSTRACT

Provided are hexaaza[3.3.3]propellane compounds represented by the following formula (I), which can be used as a main skeleton structure for novel molecular explosives and method for preparing the same:

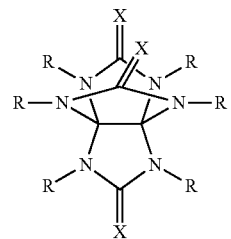

[Formula I]

Figure 1:
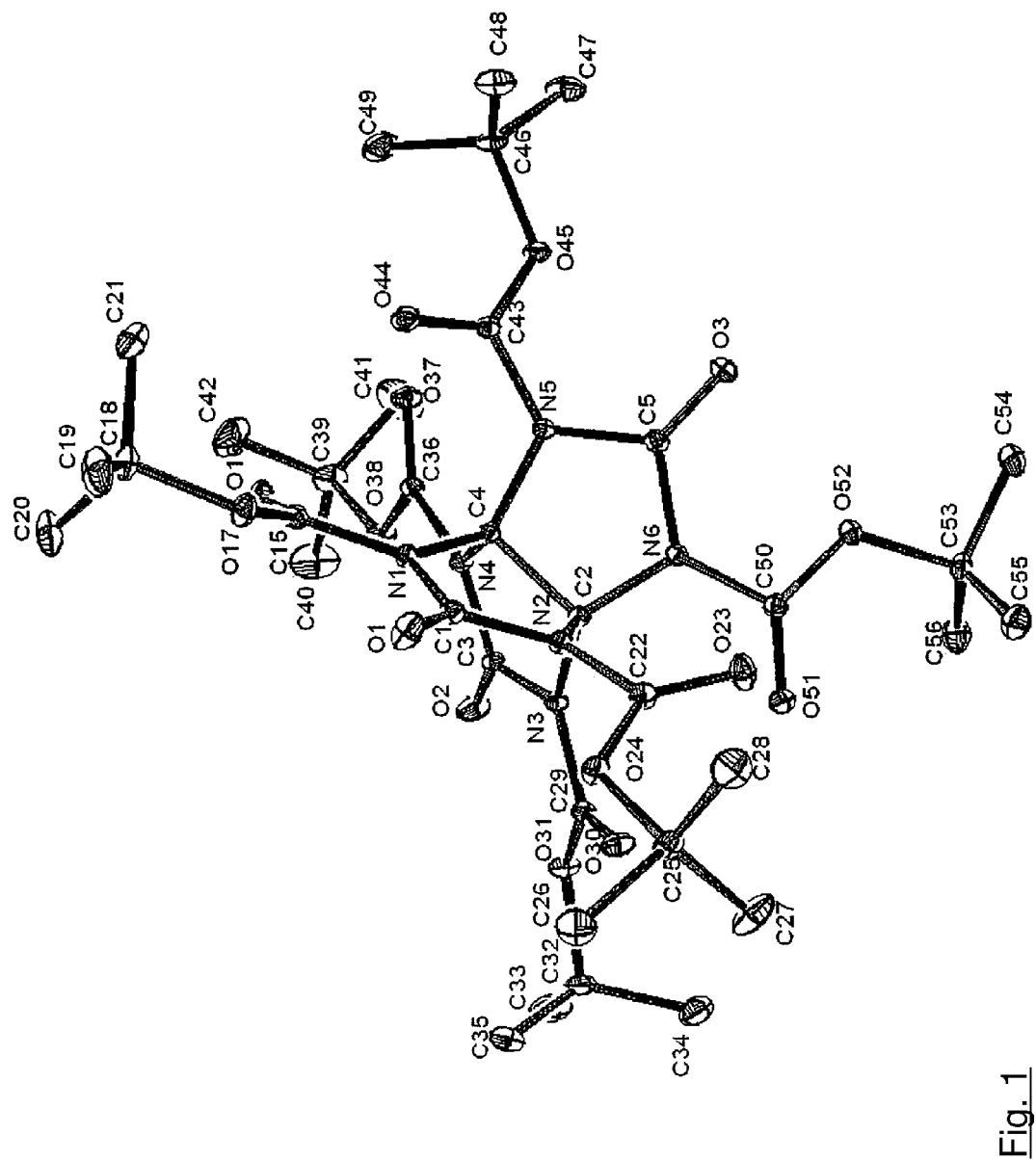

wherein, R is H, $C_1$-$C_{20}$ alkyl, cycloalkyl, arylalkyl or aryl, which may contain heteroatoms such as oxygen, nitrogen, sulfur, halogen, etc. or unsaturations; and X is $H_2$, O or S.

6 Claims, 3 Drawing Sheets

HEXAAZA [3.3.3] PROPELLANE COMPOUNDS AS KEY INTERMEDIATES FOR NEW MOLECULAR EXPLOSIVES AND A METHOD FOR PREPARING THE SAME

CROSS-REFERENCE TO RELATED APPLICATION

This application claims the benefit and priority of Korean Patent Application No. 10-2012-0085155 filed Aug. 3, 2012. The entire disclosure of the above application is incorporated herein by reference.

TECHNICAL FIELD

The present invention relates to a main carbon-nitrogen skeleton structure of hexanitrohexaaza[3.3.3]propellane compounds which can be used as a novel molecular explosive, particularly, novel hexaaza[3.3.3]propellane compounds and a method for preparing the same.

BACKGROUND OF THE INVENTION

It has been reported that, among high density, polycyclic insensitive molecular explosives developed in the developed countries including the United States, etc., compounds known to have most detonating power are hexanitrohexaazaisowurtzitane (HNIW) compounds having an isowurtzitane structure and octanitrocubane (ONC) having a cubane structure, and the explosive properties thereof are well-known to be considerably superior to the commercially available HMX or RDX. From the various studies conventionally made on such compounds, it has been learned that compounds having high atomic density in ring structure have an advantageous effect on the explosive properties, however, conventional methods for preparing HNIW or ONC compounds have some problems such as the requirement of complex procedure consisting of various steps or low yield. Therefore, for developing compounds having great ring strain and high atomic density such as HNIW or ONC, the present inventors have come with an idea of preparing compounds having a propellane structure that has three rings, and particularly [3.3.3]propellane was considered to be a possible candidate for suitable synthesis since it has 28 kcal/mol of ring strain energy of molecule which suggests its relatively high potential energy and −30 Kcal/mol of enthalpy ($\Delta H_f$(kcal/mol)) which means stable to synthesis. Based on this, azapropellane compounds which have a [3.3.3]propellane structure substituted with various numbers of nitrogen atoms have been considered. There are hardly examples of such azapropellane structure compounds synthesized or applied as a high energy material, and particularly for hexaaza[3.3.3]propellane there have not been any examples disclosing its synthesis or use.

SUMMARY OF THE INVENTION

The purpose of the present invention is to provide hexaaza[3.3.3]propellane as a main skeleton structure in hexanitrohexaaza[3.3.3]propellane that is a novel high-density polycyclic insensitive molecular explosive, giving high energy when applied as a molecular explosive, wherein the propellane skeleton structure is substituted by 6 nitrogen atoms, and a method for preparing the same.

DETAILED DESCRIPTION OF THE INVENTION

According to the present invention, a hexaaza[3.3.3]propellane compound represented by the following formula (I) which is a key structure of a novel high energy material used as molecular explosives.

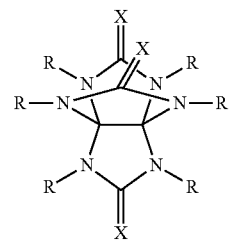

[Formula I]

wherein, R is H, $C_1$-$C_{20}$ alkyl, cycloalkyl, arylalkyl or aryl, wherein the alkyl or aryl may contain heteroatoms such as oxygen, nitrogen, sulfur, etc., or unsaturations; and X is $H_2$, O or S.

The present invention provides a method for preparing hexaaza[3.3.3]propellane compounds represented by the above formula (I), and specifically a method for preparing compounds having a structure of hexaaza[3.3.3]propellane, represented by the compounds (3), (4), (5), (6) and (7) in the following reaction scheme.

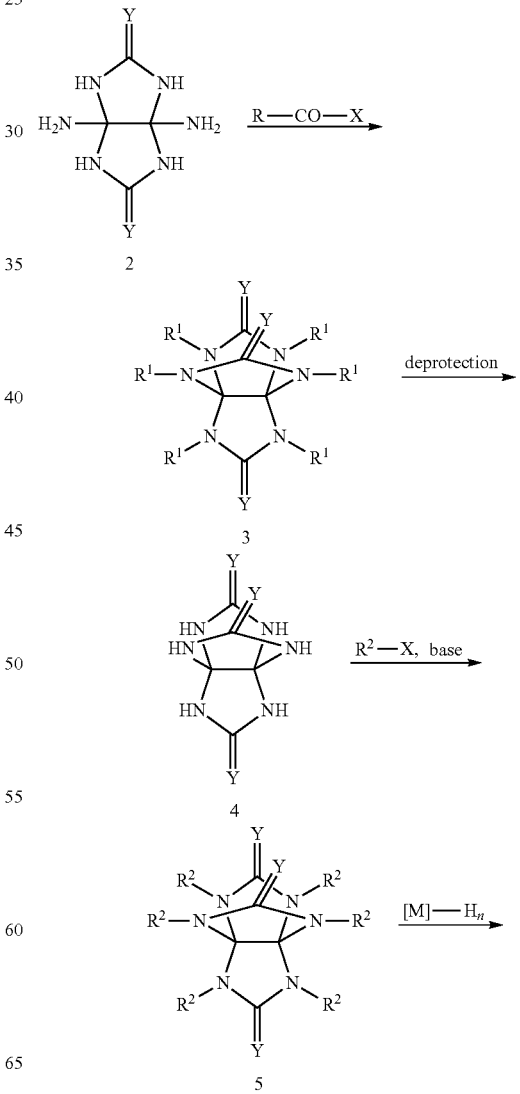

[Reaction scheme 1]

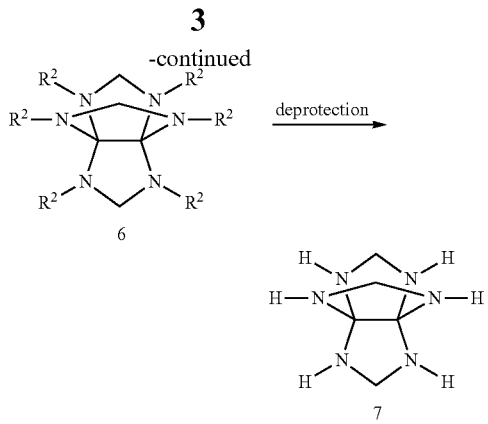

In the above reaction scheme 1, Y is O or S; $R^2$ and $R^2$ are, although these are not specifically limited as long as these are organic functional group generally applicable as amine protecting groups, for example $C_1$-$C_{20}$ alkyl, cycloalkyl, arylalkyl or aryl, which may contain heteroatoms such as oxygen, nitrogen, sulfur, halogen, etc. or unsaturations.

More specifically, by the method for preparing hexaaza [3.3.3]propellane compounds represented by the above formula (I) according to the present invention, as represented in the above reaction scheme 1, a method for preparing a compound having a hexaaza[3.3.3]propellane structure as represented by the compound (3), wherein the X is O or S in the above formula (I), is provided.

In the above reaction scheme 1, as for the compound (2), glycoluril diamine(in this case, Y=O), which may be prepared by reacting $K_3Fe(CN)_6$ with ammonium hydroxide from uric acid, may be used.

By introducing a carbonyl group into the compound (2) by using R—CO—X reagent, it is possible to prepare the compound (3), one of the compounds having a hexaaza[3.3.3] propellane structure. In the chemical formula R—CO—X for the reagent, R is H, or $C_1$-$C_{20}$ alkyl, cycloalkyl, alkoxy, arylalkyl or aryl, which may contain heteroatoms such as oxygen, nitrogen, sulfur, chlorine and the like or unsaturations; and X is Cl, Br, I, H, or $C_1$-$C_{20}$ alkyl, cycloalkyl, alkoxy, arylalkyl or aryl, which may be the same or different from R and may contain heteroatoms such as oxygen, nitrogen, sulfur, etc. or unsaturations. The specific species of the reagent having the structure of R—CO—X corresponding to the above definition may be optionally selected and used by an ordinarily skilled person in the art. For example, mentioned may be: formates such as benzyl chloroformate, etc.; carbonates such as di-tert-butyl dicarbonate; ureas such as carbonyldiimidazole; carbamates; phosgene such as triphosgene, etc.; aldehydes such as formaldehyde, etc.

The introduction of a carbonyl group may be carried out by using reaction conditions generally known in this field of art, for example at room temperature or temperature under reflux conditions for 1 hour or more, optionally with a conventionally used suitable base or acid auxiliary reagent, when necessary.

According to the method for preparing hexaaza[3.3.3]propellane compounds represented by the above formula (I) of the present invention, as represented in the above reaction scheme 1, a method for preparing a compound having a hexaaza[3.3.3]propellane structure as represented by compounds (4), (5), (6) or (7), wherein the X is O, S or H in the above formula (I), is provided.

In the compound (3) having the hexaaza[3.3.3]propellane structure as prepared by the above reaction scheme 1, the protecting group thereof may be rather easily converted when necessary, as it is further described in detail as below. Accordingly, it is possible to prepare various compounds such as compounds (4), (5), (6) and (7) from compound (3) as represented in the above reaction scheme 1 and it is further illustrated in the following descriptions.

In the preparation of the compounds shown in the above reaction scheme 1, the preparation of compounds (4), (5), (6) and (7) from compound (3) comprises the following steps: removing organic functional groups($R^1$) bound to nitrogen from the compound (3), i.e. deprotection of nitrogen, to prepare the compound (4); protection of the nitrogen again by reacting the resulted compound (4) with an organic compound($R^2$—X) to prepare the compound (5); reduction of Y(carbonyl or thiocarbonyl) of the compound (5) by using [M]-$H_n$ to prepare the compound (6); and removing the organic functional groups($R^2$) from the compound (6), i.e. deprotection of nitrogen, to prepare the compound (7).

More particularly, in the preparation of the compounds shown in the above reaction scheme 1, the preparation of the compound (4) from the compound (3) is carried out by the deprotection of nitrogen, wherein the organic functional groups $R^1$ bound to the nitrogen of the compound (3) are removed. The deprotection may be carried out by using a metal catalyst such as copper, Cesium, iron, haloaluminum, samarium, magnesium, ytterbium, titanium, tin or the like or a non-metal catalyst, under the presence of suitable organic or inorganic acids including hydrochloric acid, sulfuric acid, nitric acid, acetic acid and trifluoroacetic acid, etc.; or under the presence of organic or inorganic bases including a sodium hydroxide solution, an ammonia solution, hydride, and tertiary amine, etc.; or under neutral conditions, depending on the functional groups($R^1$) in the compound (3). The deprotection conditions or catalysts are not particularly limited and may be suitably selected by an ordinarily skilled person in the art depending on the functional groups intended to be removed.

In the preparation of the compounds represented in the above reaction scheme 1, the preparation of the compound (5) from the compound (4) may be carried out by introducing protecting groups into the amine groups of the compound (4) via the reaction of the compound (4) with a compound represented by $R^2$—X which provides protecting groups. In $R^2$—X, $R^2$ is $C_1$-$C_{20}$ alkyl, cycloalkyl, arylalkyl or aryl, which may contain heteroatoms such as oxygen, nitrogen, sulfur, halogens, etc. or unsaturations, although $R^2$ is not specifically limited as long as it is a generally applicable amine protecting group; and X is Cl, Br, I, H, or, which may be different from or same with $R^2$, $C_1$-$C_{20}$ alkyl, cycloalkyl, alkoxy, arylalkyl or aryl, which may contain oxygen, nitrogen, sulfur, halogen, etc, or unsaturations. As for the bases used in the procedure of introducing protecting groups into the compound (4), any organic or inorganic bases such as sodium hydride, sodium hydroxide, lithium hydroxide, butyl lithium, potassium carbonate, sodium carbonate, sodium bicarbonate, lithium dialkylamine may be used. The protecting group introducing conditions or bases used therefore is not specifically limited and may be suitably selected by an ordinary skilled person in the art.

In the meantime, in the compound (5) shown in the above reaction scheme 1, Y may be O or S, and as shown in the reaction scheme 2 as below, when Y is O (i.e., carbonyl group), Y may be substituted with S(i.e, thiocarbonyl group) by using Lawesson reagent or the like under reflux conditions, as similar cases are known in this field of art. The definition of $R^2$ is same as the definition of $R^2$ made in relation with the $R^2$—X used in the preparation of the compound (5) in the above reaction scheme 1. As for the substitution step, any conventional substitution method which can be suitably carried out by an ordinary skilled person in the art may be used without specific limitations. For example, the substitution may be carried out by using Lawesson's reagent under the reflux conditions of suitable solvent such as benzene, etc.

[Reaction scheme 2]

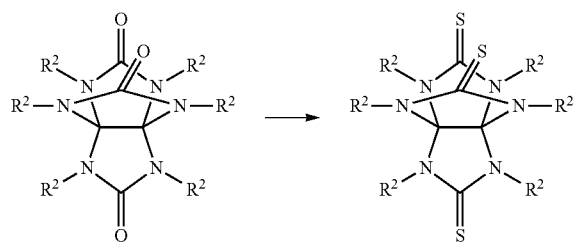

In the preparation of the compound represented in the above reaction scheme 1, the preparation of compound (6) from the compound (5) may be carried out by reducing Y which is a carbonyl group or a thiocarbonyl group by using [M]—H$_n$, as shown in the above reaction scheme 1, wherein M is selected from a group of metal consisting of an aluminum, boron or the like, and n is an integer of 1-4. Specifically, for example, the reducing agent, [M]-H$_n$ may be any one selected from the group consisting of boron hydride, lithium borohydride, sodium borohydride, aluminum hydride, sodium aluminum hydride, lithium aluminum hydride, sodium cyanoborohydride, sodium dialkylamine borohydride, dialkyl aluminum hydride and Raney nickel. The reduction process may be carried out by using such reducing agent alone or together with any one selected from the group consisting of iodine, sulfuric acid, titanium chloride, aluminum chloride, tin chloride, zinc and triethylether tetrafluoro borate.

In the preparation of the compound represented in the above reaction scheme 1, the preparation of compound (7) from the compound (6) may be carried out by deprotection the compound (6), similar to the method described in relation with the preparation of the compound (4) from the compound (3). The deprotection may be carried out by using a metal catalyst such as copper, cesium, iron, haloaluminum, samarium, magnesium, ytterbium, titanium, tin or the like or a non-metal catalyst, under the presence of suitable organic or inorganic acids including hydrochloric acid, sulfuric acid, nitric acid, acetic acid and trifluoroacetic acid, etc.; or under the presence of organic or inorganic bases including a sodium hydroxide solution, an ammonia solution, a hydride, and tertiary amine, etc.; or under neutral conditions, depending on the functional groups(R$^2$) in the compound (6). The deprotection conditions or catalysts are not particularly limited and may be suitably selected by an ordinarily skilled person in the art depending on the functional groups intended to be removed.

The structure of thus obtained hexaazatricyclo[3.3.3]undecane compounds can be confirmed by using spectroscopic data such as NMR, etc. and X-ray diffraction analysis.

EFFECT OF THE INVENTION

According to the present invention, a method for preparing a hexaaza[3.3.3]propellane compound that is the key structure of hexanitrohexaazapropellane compounds which is a novel, high-density, polycyclic insensitive molecular explosive is provided. Since the protecting groups in the obtained hexaaza[3.3.3]propellane compounds may be optionally converted upon necessity, introduction of nitro groups or application of suitable protecting groups so as to prepare other similar compounds can be suitably made upon given circumstances, thereby advantageously carrying out smooth synthesis of desired compounds. Moreover, it has further advantages of providing great potential energy much higher than that of other conventional molecular explosives, when used as a skeleton. Further, life of the molecular explosive compounds according to the present invention is anticipated to be at least 20 years as much as other conventional molecular explosives.

BRIEF DESCRIPTION OF THE INVENTION

Figure 2:
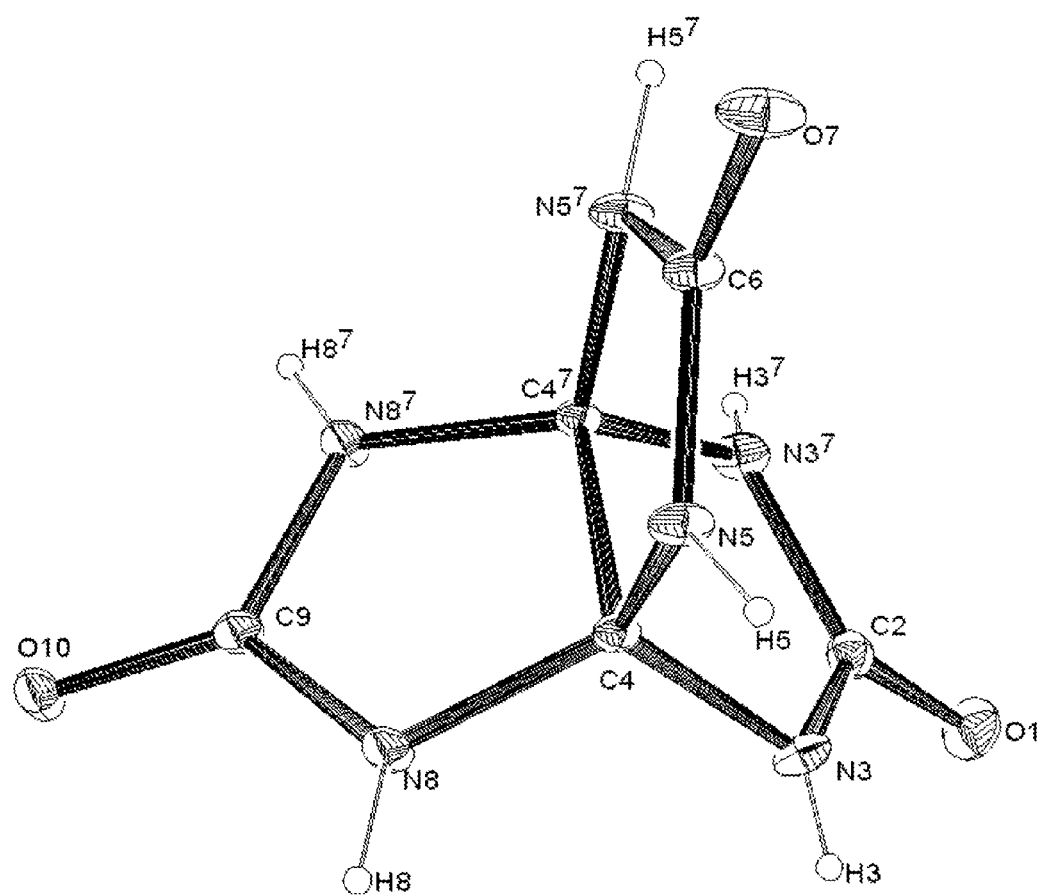
Figure 3:
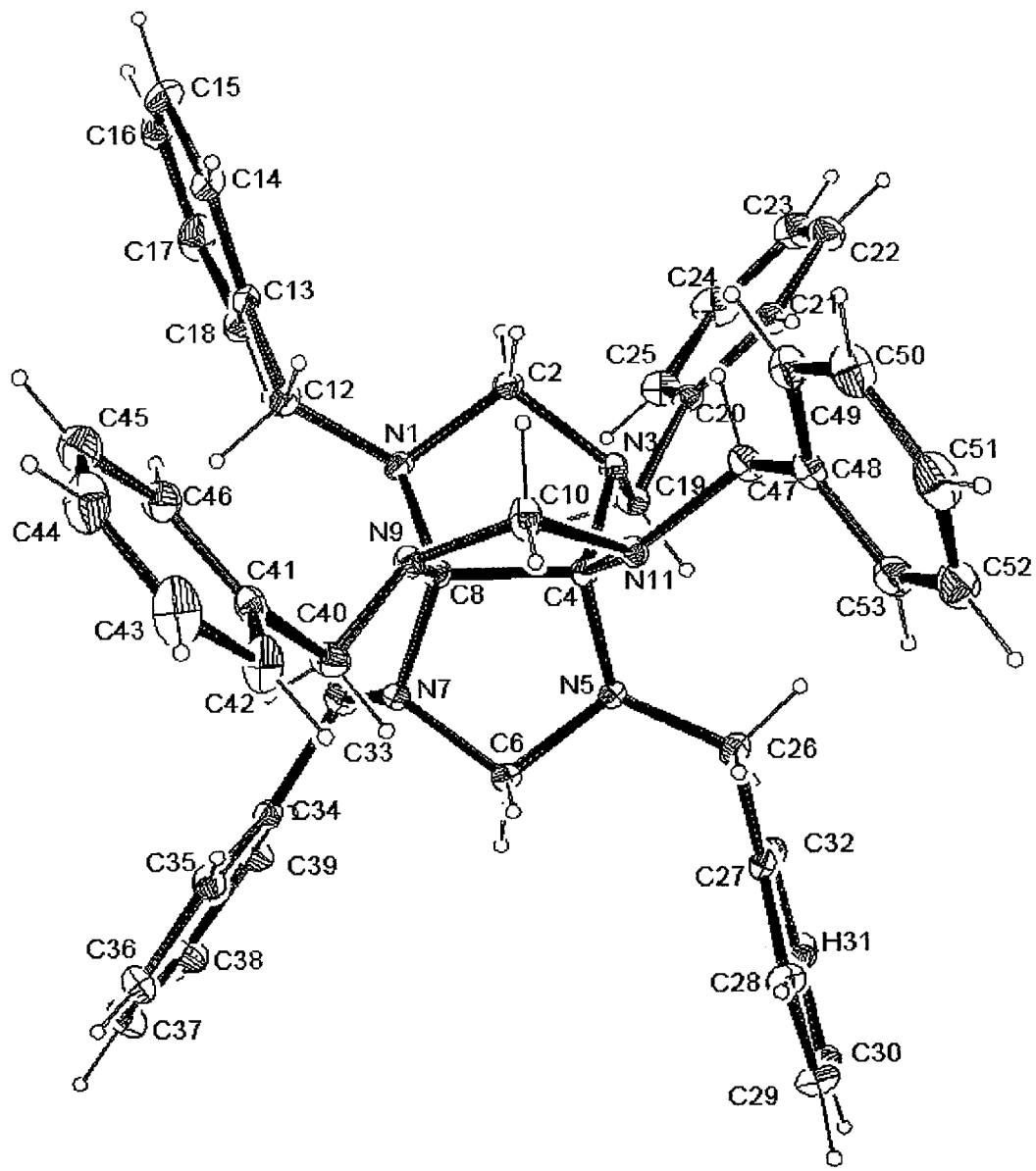

FIGS. 1, 2 and 3 show the results of X-ray diffraction analysis of the compounds from Examples 1, 2 and 4, respectively.

PREFERRED EMBODIMENT OF THE INVENTION

Hereinafter, the present invention is further described in detail by way of the following examples, however the present invention is by no means restricted by the examples given below.

Reagents and Materials

Potassium ferricyanide (K$_3$Fe(CN)$_6$), di-tert-butyl dicarbonate(Boc$_2$O), triethylamine (TEA), N,N-dimethylamino pyridine (DMAP), benzyl bromide, allyl bromide, sodium hydride(NaH) and lithium aluminum hydride (LAH) were commercially available from Sigma-Aldrich. Solvents such as trifluoroacetic acid, ammonium hydroxide, acetone, ethanol, tetrahydrofuran, dimethylsulfoxide, N,N-dimethyl formamide and methylene chloride were commercially available from OCI and Dae-Jung company in South Korea.

Example 1

Preparation of 2,4,6,8,9,11-hexa-N-Boc-3,7,10-trioxo-2,4,6,8,9,11-hexaaza[3.3.3]propellane (3')

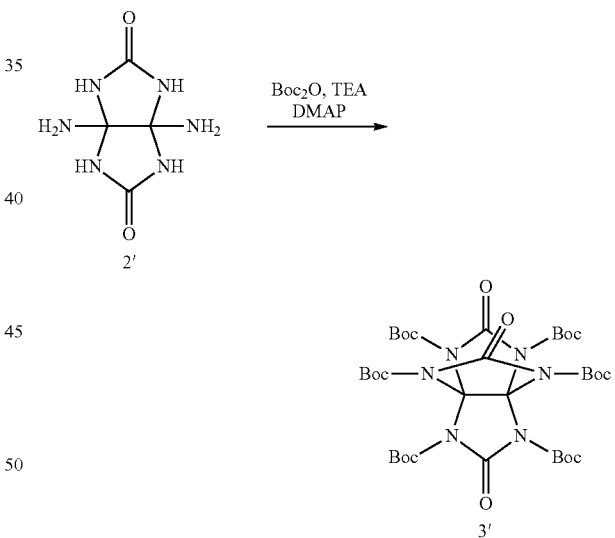

As shown in the above reaction scheme, glycoluril diamine (2')(0.5 g, 2.90 mmol) and di-tert-butyl dicarbonate (6.7 mL, 29.04 mmol) were dissolved in dimethylsulfoxide (2 mL). N,N-dimethylamino pyridine (1.42 g, 11.62 mmol) was slowly added and the resulting mixture was stirred at room temperature for 6 hours. After the reaction, the product was extracted with diethyl ether and water. The organic phase was removed under reduced pressure and purified by silica gel column chromatography(hexane:ethyl acetate=4:1 was used as eluent). White solid compound (1.88 g, yield 81%) was obtained and this compound was crystallized in methylene chloride. The crystal structure of the obtained compound (3') was analyzed by X-ray diffraction and the results were shown in FIG. 1.

NMR results:
$^1$H NMR (CDCl$_3$) δ 1.54 (s, 54H)
$^{13}$C NMR (CDCl$_3$) δ 147.6, 144.4, 85.2, 83.2, 27.8
IR (KBr) $v_{max}$: 2938, 2936, 2045, 1802, 1775, 1628, 1475, 1458 cm$^{-1}$
Element analysis results:
Calculated value: C-52.62, H-6.81, N-10.52
Measured value: C-52.57, H-7.06, N-10.12

Example 2

Preparation of 3,7,10-trioxo-2,4,6,8,9,11-hexaaza [3.3.3]propellane(4')

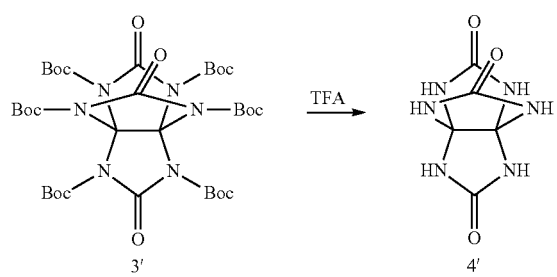 [SMILES: CC(C)(C)OC(=O)N1C(=O)N(C(=O)OC(C)(C)C)C23N(C(=O)OC(C)(C)C)C(=O)N(C(=O)OC(C)(C)C)C12N(C(=O)OC(C)(C)C)C(=O)N3C(=O)OC(C)(C)C ; O=C1NC23NC(=O)NC2(N1)NC(=O)N3]

As shown in the above reaction scheme, to the compound (3') (1.0 g, 1.25 mmol) obtained from the above example 1, trifluoroacetic acid (9 mL) was slowly added dropwise at room temperature until not bubbling. The resulting mixture was stirred for 1 h and the reaction solvent was removed by evaporation under reduced pressure. Ethanol (20 mL) was added to the residue and the precipitates were filtered, washed with acetone and dried to obtain a product as a white solid (0.25 g, yield: 99%). This solid was recrystallized with dimethyl sulfoxide to obtain needle-shaped colorless crystal and its structure was confirmed by X-ray diffraction analysis, the results of which were shown in FIG. 2.
NMR results:
$^1$H NMR (DMSO-d$_6$) δ 8.06 (s, 6H)
$^{13}$C NMR (DMSO-d$_6$) δ 159.4, 85.2
IR (KBr) $v_{max}$: 3217, 2830, 1748, 1688, 1524, 1473 cm$^{-1}$
HRMS (FAB): for C$_5$H$_7$N$_6$O$_3$ [M]+, calculated value: 199.0574,
measured value: 199.0584
Element analysis results:
Calculated value: C-30.31, H-3.05, N-42.41
Measured value: C-30.70, H-3.33, N-42.39

Example 3

Preparation of 2,4,6,8,9,11-hexa-N-benzyl-3,7,10-trioxo-2,4,6,8,11-hexaaza[3.3.3]propellane (5')

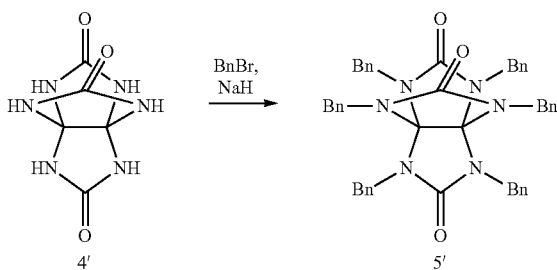 [SMILES: O=C1NC23NC(=O)NC2(N1)NC(=O)N3 ; O=C1N(Cc2ccccc2)C23N(Cc4ccccc4)C(=O)N(Cc4ccccc4)C2(N1Cc1ccccc1)N(Cc1ccccc1)C(=O)N3Cc1ccccc1]

As shown in the above reaction scheme, the compound (4') (0.7 g, 3.53 mmol) obtained from the above example 2 was dissolved in a mixture of N,N-dimethyl formamide (4 mL) and dimethyl sulfoxide (1 mL) under nitrogen atmosphere, then benzyl bromide (3.4 mL, 28.28 mmol) was added to the mixture and the reaction temperature was cooled to 0° C. or less. After 5 minutes of stirring, sodium hydride (1.13 g, 28.28 mmol) was slowly added to the reaction mixture. The reaction temperature was slowly raised up to room temperature and stirred for additional 6 hours. When the reaction was completed, the temperature was re-cooled to 0° C., and extracted with an aqueous solution of ammonium chloride and diethyl ether. The organic phase was evaporated under reduced pressure and then purified by silica gel chromatography (hexane:ethyl acetate=4:1 was used as eluent) to obtain a product, i.e. the compound (5') as represented in the above scheme, as a white solid (1.28 g, yield: 49%).
NMR results:
$^1$H NMR (CDCl$_3$) δ 7.32-7.27 (m, 18H), 7.12-7.09 (m, 12H), 4.32 (s, 12H)
$^{13}$C NMR (CDCl$_3$) δ 157.3, 136.8, 128.8, 127.7, 126.6, 89.5, 45.8
IR (KBr) $v_{max}$: 3086. 3059. 2693, 2927, 1718, 1472, 1450, 1421 cm$^{-1}$
HRMS (FAB+): for C$_{47}$H$_{42}$N$_6$O$_3$ [M]+, calculated value: 739.3391, measured value: 739.3395
Element analysis results:
Calculated value: C-76.40, H-5.73, N-11.37
Measured value: C-76.24, H-5.89, N-11.57

Example 4

Preparation of 2,4,6,8,9,11-hexa-N-benzyl-2,4,6,8, 11-hexaaza[3.3.3]propellane (6')

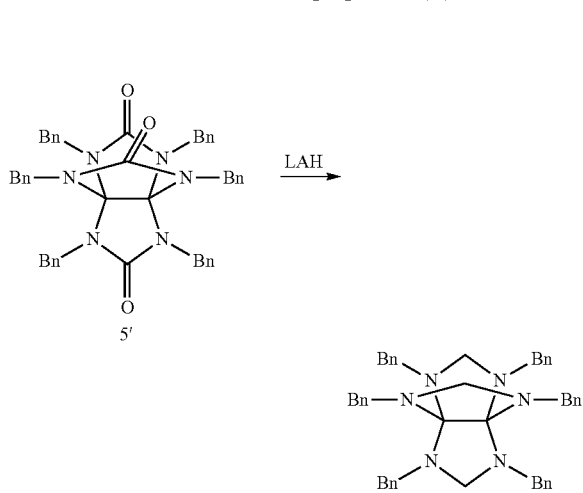

As shown in the above reaction scheme, tetrahydrofuran (7 mL) was slowly added to LAH(0.46 g, 12.20 mmol) in 0° C. cooled flask under N$_2$ mood. The compound (5') obtained from the above example 3 was slowly added and stirred. After 40 minutes, the temperature of the resulted solution was slowly raised up to room temperature (20° C.) and stirred at 40° C. for 12 hours. After the reaction, the temperature was re-cooled to 0° C. or less and stirred. After 5 minutes, ethyl acetate (15 mL) was slowly added and stirred for 30 minutes. The resulted solution was filtered subsequently through a celite pad and a silica gel pad and the filtered solvent was removed under reduced pressure to obtain a white solid (6') (0.38 g, yield: 81%) as represented in the above reaction scheme. The product was crystallized in methylene chloride for X-ray diffraction analysis.

NMR results:

$^1$H NMR (CDCl$_3$) δ 7.18-7.41 (m, 30H), 4.16 (s, 12H), 3.75 (s, 6H)

$^{13}$C NMR (CDCl$_3$) δ 140.2, 128.3, 128.1, 126.7, 108.9, 76.5, 52.2

Element analysis results:

Calculated value: C-81.00, H-6.94, N-12.06

Measured value: C-81.01, H-6.99, N-11.92

What is claimed is:

1. A Hexaaza[3.3.3]propellane compound represented by Formula 1:

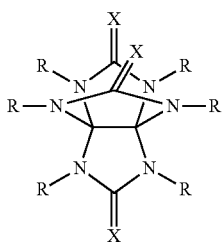

Formula 1 wherein R is H, C$_1$-C$_{20}$ alkyl, cycloalkyl, arylalkyl or aryl, wherein the alkyl or aryl optionally contains heteroatoms selected from oxygen, nitrogen, and sulfur or halo substitutions, and X is H$_2$, O or S.

2. A method for preparing a hexaaza[3.3.3]propellane compound represented by Formula 3, which comprises introduction of a carbonyl group into a compound of Formula 2 by using a compound represented by R—CO—X:

Formula 2

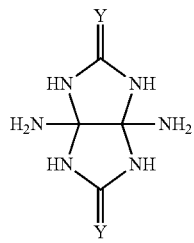

in Formula 2, Y is O or S;

Formula 3

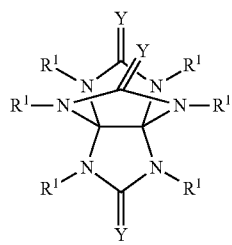

in Formula 3, R$^1$ is C$_1$-C$_{20}$ alkyl, cycloalkyl, arylalkyl or aryl, which optionally contains heteroatoms selected from oxygen, nitrogen, and sulfur or halo substitutions, and Y is O or S; and in the above R—CO—X compound, R is H, C$_1$-C$_{20}$ alkyl, cycloalkyl, alkoxy, arylalkyl, or aryl, which optionally contains heteroatoms selected from oxygen, nitrogen, and sulfur or halo substitutions, and X is Cl, Br, I, H, C$_1$-C$_{20}$ alkyl, cycloalkyl, alkoxy, arylalkyl, or aryl, which optionally contains heteroatoms selected from oxygen, nitrogen, and sulfur or halo substitutions.

3. A method for preparing a hexaaza[3.3.3]propellane compound represented by Formula 4, which comprises a deprotecting step wherein the protecting group of a hexaaza[3.3.3]propellane compound represented by Formula 3 is removed by using a metal or non-metal catalyst:

Formula 3

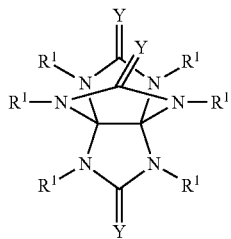

in Formula 3, R$^1$ is C$_1$-C$_{20}$ alkyl, cycloalkyl, arylalkyl or aryl, which optionally contains heteroatoms selected from oxygen, nitrogen, and sulfur or halo substitutions; and Y is O or S; and Formula 4

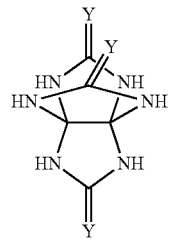

in the above formula, Y is O or S.

4. A method for preparing a hexaaza[3.3.3]propellane compound represented by Formula 5, which protecting groups introduced to a compound of Formula 4 below by the reaction of the compound of Formula 4 with a reagent represented by R$^2$—X at the presence of a base, wherein R$^2$—X, R$^2$ is C$_1$-C$_{20}$ alkyl, cycloalkyl, arylalkyl or aryl, which optionally contains heteroatoms selected from oxygen, nitrogen, and sulfur or halo substitutions; and X is Cl, Br, I, H, C$_1$-C$_{20}$ alkyl, cycloalkyl, alkoxy, arylalkyl or aryl, which optionally contains heteroatoms selected from oxygen, nitrogen, and sulfur or halo substitutions:

Formula 4

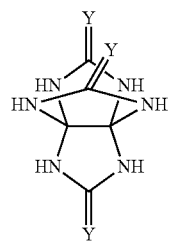

in the above formula, Y is O or S; and

Formula 5

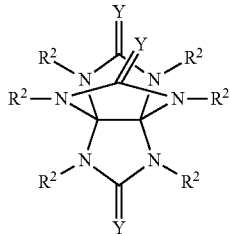

in the above formula, $R^2$ is $C_1$-$C_{20}$ alkyl, cycloalkyl, arylalkyl or aryl, which optionally contains heteroatoms selected from oxygen, nitrogen, and sulfur or halo substitutions; and Y is O or S.

5. A method for preparing hexaaza[3.3.3]propellane compound represented by Formula 6, which comprises reducing Y in the hexaaza[3.3.3]propellane compound represented by Formula 5 by using $[M]$-$H_n$, wherein M is selected from a group consisting of aluminum and boron and n is an integer of 1-4:

Formula 5

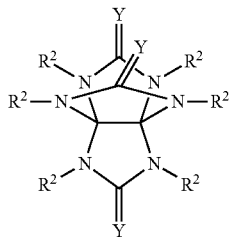

in the above formula, $R^2$ is $C_1$-$C_{20}$ alkyl, cycloalkyl, arylalkyl or aryl, which optionally contains heteroatoms selected from oxygen, nitrogen, and sulfur or halo substitutions; and Y is O or S;

Formula 6

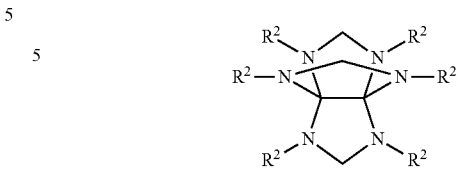

in the above formula, $R^2$ is $C_1$-$C_{20}$ alkyl, cycloalkyl, arylalkyl or aryl, which optionally contains heteroatoms selected from oxygen, nitrogen, and sulfur or halo substitutions.

6. A method for preparing a hexaaza[3.3.3]propellane compound represented by Formula 7, which comprises a deprotecting step wherein the protection group $R^2$ in the hexaaza[3.3.3]propellane compound represented by Formula 6 is removed by a metal or non-metal catalyst:

Formula 6

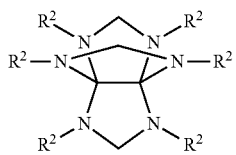

in the above formula, $R^2$ is $C_1$-$C_{20}$ alkyl, cycloalkyl, arylalkyl or aryl, which optionally contains heteroatoms selected from oxygen, nitrogen, and sulfur or halo substitutions;

Formula 7

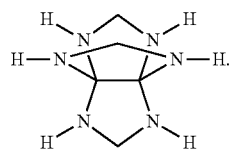

* * * * *